Nov. 20, 1934. G. D. AIKEN Plant Pat. 112
STRAWBERRY
Filed April 16, 1934
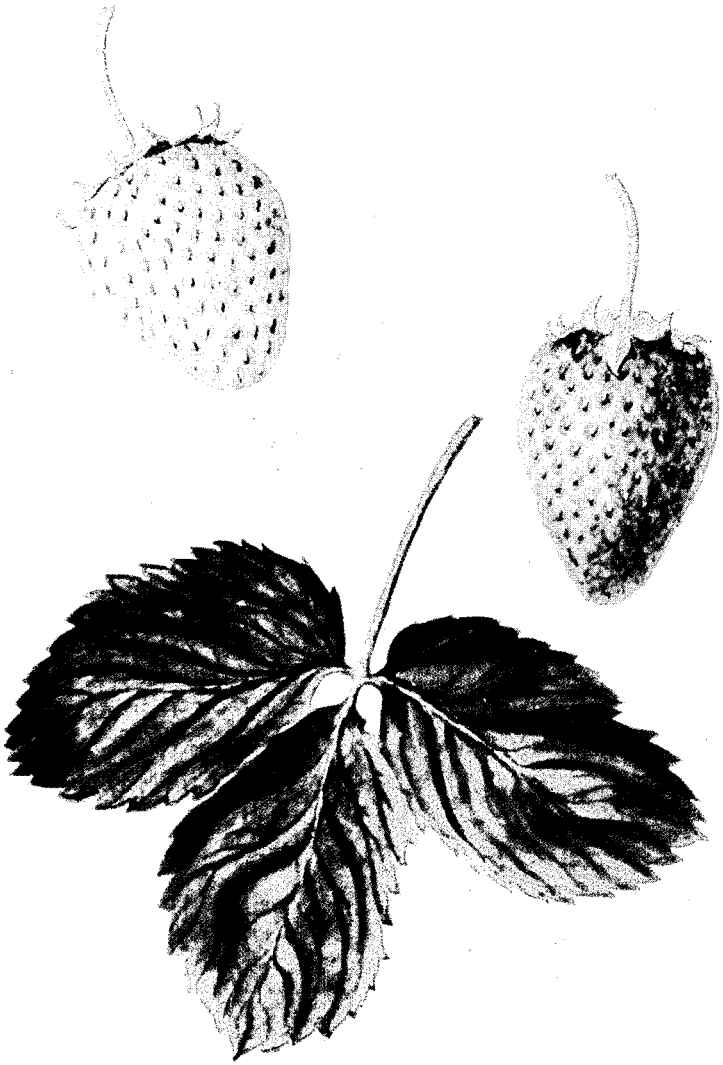
INVENTOR
George D. Aiken
By Orville M. Kile
PLANT PATENT AGENT Patented Nov. 20, 1934

Plant Pat. 112

UNITED STATES PATENT OFFICE

112

STRAWBERRY

George D. Aiken, Putney, Vt.

Application April 16, 1934, Serial No. 720,897

1 Claim. (Cl. 47—62)

My invention relates to improvements in so-called everbearing strawberries. The object of my invention is to provide a variety of strawberry of the type mentioned, suitable for commercial use, producing fall fruit of superior quality, being apparently immune from disease and readily propagated as well as having other desirable characteristics. A distinguishing feature is the fact that the summer fruit is quite different in shape, sige and quality from that produced in the fall.

My new variety is the result of a cross between the "Howard 17" and the "Superb" and partakes of certain characteristics of each. The summer crop of berries resembles Superb while the fall crop resembles Howard 17.

The first plant of this new variety came into bearing in 1927. I have since tested it both on my own grounds and at several State agricultural experiment stations.

The accompanying illustration shows in full color a leaf branch of the new variety, a typical fall berry (at right) and a typical summer berry (at left).

The following is a detailed description of the principal features and characteristics;

The plant is a very strong grower, healthy and apparently immune from disease. It is a freer plant maker than any other everbearing strawberry known to me in this latitude. Its normal habit of growth is in double crown form, but sometimes produces several crowns per plant.

This variety produces an enormous crop of summer fruit, in fact it has a tendency to overbear for the summer crop, being similar to the variety Superb in this respect.

The ripening date for the early crop is described as mid-season, being nearly a week later than the Howard 17 variety. It fruits continuously throughout the summer if permitted to do so. Two-year-old plants fruit heavily in the fall and if they are not permitted to bear a heavy summer crop they make as many new plants the second year as they do the first. This is a distinct advantage over other everbearing strawberries.

The best fall berries are produced in this latitude between September 15 and October 15.

*Foliage.*—Plentiful, light green in color, leaves medium in size and having deep-notched edges, heavily veined. The ends of the leaves are inclined to be rounded rather than pointed.

*Calyx.*—Usually consists of a single row of sepals, narrow and curling sufficiently to be easily removed from the ripe berries. The fall berries have 12 or 14 sepals.

*Stems* are long and covered with fine hairs.

*Flowers* are "perfect" or self-pollenizing.

*Berries.*—The summer crop of berries resembles the variety "Superb", typical specimens being about 1¼ inches long, rather conical in form with the apex considerably rounded. Berries are borne in clusters attached to a particularly strong central stem or stalk.

The fall berries are considerably longer and more pointed in shape, being 1½ to 1⅝ inches long. The largest circumference or girth of the fall berries occurs farther down the berry below the calyx than is the case with the more nearly conical-shaped berry.

The berries are a deep dark red on the side facing the sun and somewhat lighter on the reverse side. The red color extends entirely through the meat of the berry.

The seeds are large and prominent, their bright yellow color on the side away from the sun standing out in sharp contrast with the red background. On the side facing the sun, however, the seeds assume a much darker color which more nearly blends in with the dark red background.

*Flavor.*—The quality of the fruit is excellent, particularly the fall berries which outrank most other fall varieties in this respect.

The specifications herewith set forth the general characteristics of my new everbearing strawberry, but it must be understood that these specifications will vary somewhat with variations in seasons, cultivation and other factors.

What I claim as new is:

The new and distinct variety of so-called everbearing strawberries shown and described, characterized particularly by its fall crop of berries of large size, long pointed shape and superior quality as compared not only with the summer crop but with other known varieties.

GEORGE D. AIKEN.